United States Patent [19]

Kim et al.

[11] Patent Number: 5,703,097

[45] Date of Patent: *Dec. 30, 1997

[54] 5-PYRROLYL-2-PYRIDYLMETHYLSULFINYL BENZIMIDAZOLE DERIVATIVES

[75] Inventors: Su Ung Kim; Dong Yeon Kim, both of Seoul; Gi ju Chung, Puchun; Sung Kol Hong, Suwon; Sung Jun Park, Seoul; Sang Hoon Nam, Anyang; Yong Suk Lee, Suwon, all of Rep. of Korea

[73] Assignee: Il-Yang Pharm. Co., Ltd., Seoul, Rep. of Korea

[ * ] Notice: The term of this patent shall not extend beyond the expiration date of Pat. No. 5,554,631.

[21] Appl. No.: 537,846

[22] PCT Filed: Jul. 22, 1994

[86] PCT No.: PCT/KR94/00098

§ 371 Date: Oct. 20, 1995

§ 102(e) Date: Oct. 20, 1995

[87] PCT Pub. No.: WO95/23140

PCT Pub. Date: Aug. 31, 1995

[30] Foreign Application Priority Data

Feb. 28, 1994 [KR] Rep. of Korea ............... 3833

[51] Int. Cl.⁶ .................... C07D 401/12; A61K 31/44
[52] U.S. Cl. .................... 514/338; 546/273.7; 546/194; 544/124; 544/131; 544/364
[58] Field of Search .................... 514/338; 546/273.7; 544/124, 131, 364

[56] References Cited

U.S. PATENT DOCUMENTS

| | | |
|---|---|---|
| 4,225,431 | 9/1980 | Junggren et al. ............... 546/273.7 |
| 4,337,257 | 6/1982 | Junggren et al. ............... 546/273.7 |
| 4,508,905 | 4/1985 | Junggren et al. ............... 546/273.7 |
| 4,758,579 | 7/1988 | Kohl et al. ............... 546/273.7 |
| 5,554,631 | 9/1996 | Kim et al. ............... 514/338 |

FOREIGN PATENT DOCUMENTS

| | | |
|---|---|---|
| 0005129 | 4/1979 | European Pat. Off. . |
| 0268956 | 11/1987 | European Pat. Off. . |
| 2134523 | of 0000 | United Kingdom . |
| 1234058 | 6/1971 | United Kingdom . |

OTHER PUBLICATIONS

Chemical Abstracts, vol. 105, No. 25, issued 22 Dec. 1986 (Dec. 12, 1986) (Columbus, OH, USA) p. 797, column 2, the abstract No. 226619g, CN 105113-13-1.

Chemical Abstracts, vol. 107, No. 11, issued 14 Sep. 1987 (Sep. 13, 1987) (Colmbus, OH, USA) p. 693, column 2, the abstract No. 96720m.

Chemical Abstracts, vol. 109, No. 19, issued 7 Nov. 1988 (Nov. 7, 1988) (Columbus, OH, USA) p. 711, column 1, the abstract No. 170312q.

*Primary Examiner*—Jane Fan
*Attorney, Agent, or Firm*—Lowe, Price, LeBlanc & Becker

[57] ABSTRACT

The present invention relates to a novel compound 5-pyrrolyl-2-pyridylmethylsulfinylbenzimidazole derivative having general formula (I) and its salt,

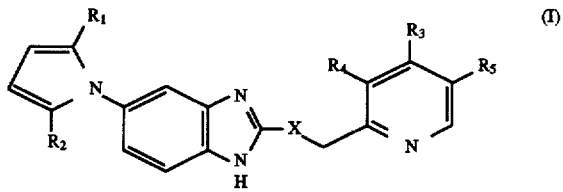

wherein all variables are as defined in the specification. The present invention also relates to a process for preparation of the compound of formula (I), as defined above, and its use as an anti-ulcer agent.

5 Claims, No Drawings

5-PYRROLYL-2-PYRIDYLMETHYLSULFINYL BENZIMIDAZOLE DERIVATIVES

This is a 371 of PCT/KR94/00098 now WO 95/23140.

TECHNICAL FIELD

The present invention relates to a novel 5-pyrrolyl-2-pyridylmethylsulfinylbenzimidazole derivative. More specifically, the present invention relates to a novel 5-pyrrolyl-2-pyridylmethylsulfinylbenzimidazole derivative represented by the following general formula (I):

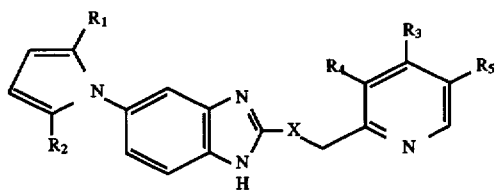

and a salt thereof, in which

X represents S, SO or $SO_2$, $R_1$ and $R_2$ independently from each other represent hydrogen or alkyl, $R_3$ represents hydrogen, $C_1$–$C_8$ alkyl, —$SR_6$, —$N(R_7)_2$, 1-piperidinyl, 4-morpholinyl, 4-methylpiperazin-1-yl, 1-pyrrolidinyl, —$OR_6$, or —$O(CH_2)_m$—Z, wherein $R_6$ represents $C_1$–$C_4$ alkyl, $C_2$–$C_4$ alkenyl, $C_3$–$C_{10}$ cycloalkyl, $C_2$–$C_5$ fluoroalkyl, or phenyl or benzyl, each of which independently substituted with one or more halogen or $C_1$–$C_4$ alkyl or alkoxy optionally substituted with halogen, $R_7$ represents hydrogen or $C_1$–$C_5$ alkyl, Z represents a group —$O(CH_2)_p$—$OR_8$, —$O(CH_2)_q$—$R_9$ or $O(CH_2)_rO(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$–$C_5$ alkyl, or when $R_4$ and $R_5$ together with the carbon atoms adjacent to pyridine ring form a ring, $R_4$ and $R_3$ or $R_3$ and $R_5$ represent —CH=CH—CH=CH—, —$O(CH_2)_n$—, —$O(CH_2)_nO$—, —$CH_2(CH_2)_n$— or —OCH=CH—, wherein n denotes an integer of 1 to 4.

The present invention also relates to a process for preparation of the compound of formula (I), as defined above, and use of the compound of formula (I) as an agent for prophylaxis and treatment of gastric and duodenal ulcers.

BACKGROUND ART

Gastric and duodenal ulcers are a gastrointestinal disease caused by various factors such as mental stress, dietary habit, intake of irritable food, and the like. The direct cause of peptic ulcers is damage to the gastric membrane due to excessive secretion of gastric acid. Accordingly, therapeutic agents which have been commonly used for treatment of the peptic ulcers includes, for example, antacids for neutralizing gastric acid, anti-pepsin agents, agents for protecting the gastric mucous membrane, anti-cholinergic agents for inhibiting gastric secretion, para-sympatholytic agents, $H_2$-receptor antagonists, and the like. At the present time, since it has been disclosed that antacids and CNS-acting antiulcerants provide only a unsatisfactory therapeutic effect and may cause adverse effects when they are administered for a long period, the use of $H_2$-receptor antagonists as agents for treating gastric and duodenal ulcers has increased.

In addition, recently 5-methoxy-2-[[(4-methoxy-3,5-dimethyl-2-pyridinyl)methyl]sulfinyl]-1H-benzimidazole (Generic name: Omeprazole) has been developed and demonstrated as a good anti-ulcer agent having a superior effect over conventional $H_2$-receptor antagonists such a cimetidine, famotidine, ranitidine and the like (see, U.S. Pat. Nos. 4,255,431, 4,337,257, 4,508,905, 4,758,579, British Patent No. 2,134,523, European Patent No. 0,005,129 and 0,268,956). Accordingly, Omeprazole is widely used in various types of formulations.

In view of the acting mechanism, contrary to conventional $H_2$-receptor antagonists, Omeprazole blocks the proton pump of $H^+,K^+$-ATPase present in the gastric membrane to inhibit the gastric secretion. In addition, Omeprazole has also an advantage of prolonged duration in comparison with conventional antiulcerants.

Thus, the present inventors have studied for a long time to develop novel anti-ulcer agents. As a result, we have synthesized a novel compound having the general formula (I), as defined above, and then identified that the compound of formula (I) as having a superior anti-ulcer effect in comparison with Omeprazole. Thus, now we have completed the present invention.

DISCLOSURE OF INVENTION

It is an object of the present invention to provide a novel 5-pyrrolyl-2-pyridylmethylsulfinylbenzimidazole derivatives having the following general formula (I):

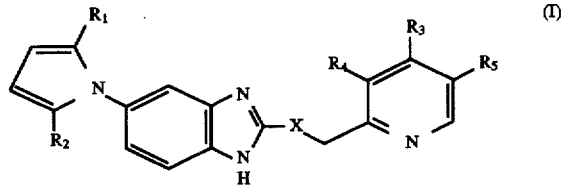

and a salt thereof, in which

X represents S, SO or $SO_2$, $R_1$ and $R_2$ independently from each other represent hydrogen or alkyl, $R_3$ represents hydrogen, $C_1$–$C_8$ alkyl, —$SR_6$, —$N(R_7)_2$, 1-piperidinyl, 4-morpholinyl, 4-methylpiperazin-1-yl, 1-pyrrolidinyl, —$OR_6$, or —$O(CH_2)_m$—Z, wherein $R_6$ represents $C_1$–$C_4$ alkyl, $C_2$–$C_4$ alkenyl, $C_3$–$C_{10}$ cycloalkyl, $C_2$–$C_5$ fluoroalkyl, or phenyl or benzyl, each of which independently substituted with one or more halogen or $C_1$–$C_4$ alkyl or alkoxy optionally substituted with halogen, $R_7$ represents hydrogen or $C_1$–$C_5$ alkyl, Z represents a group —$O(CH_2)_p$—$OR_8$, —$O(CH_2)_q$—$R_9$ or —$O(CH_2)_rO(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$–$C_5$ alkyl, or when $R_4$ and $R_5$ together with the carbon atoms adjacent to pyridine ring form a ring, $R_4$ and $R_3$ or $R_3$ and $R_5$ represent —CH=CH—CH=CH—, —O(CH$_2$)$_n$—, —O(CH$_2$)$_n$O—, —CH$_2$(CH$_2$)$_n$— or —OCH=CH—, wherein n denotes an integer of 1 to 4.

It is another object of the present invention to provide a process for preparation of the compound of formula (I):

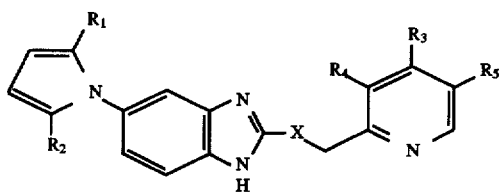

and a salt thereof, wherein X, R1, R2, R3, R4 and R5 are defined as previously described, characterized in that (a) a compound having the following general formula (II):

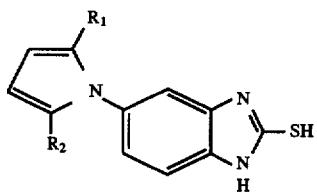

wherein $R_1$ and $R_2$ are defined as previously described, is reacted with a compound having the following general formula (III):

wherein $R_3$, $R_4$ and $R_5$ are defined as previously described and Y represents halogen, esterified hydroxy or acyloxy, in an organic solvent in the presence of a base, or (b) a compound having the following general formula (IV):

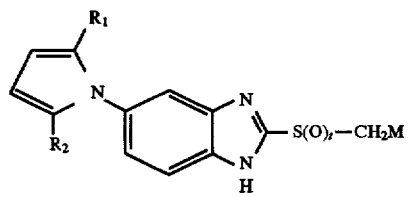

wherein $R_1$ and $R_2$ are defined as previously described, t denotes 1 or 2 and M represents an alkali metal, is reacted with a compound having the following general formula (V):

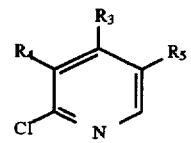

wherein $R_3$, $R_4$ and $R_5$ are defined as previously described, or (c) a compound having the following general formula (VI):

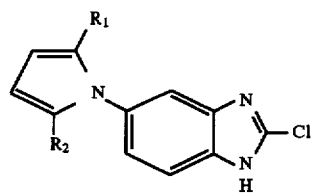

wherein $R_1$ and $R_2$ are defined as previously described, is reacted with a compound having the following general formula (VII):

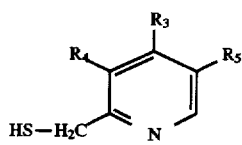

wherein $R_3$, $R_4$ and $R_5$ are defined as previously described, or (d) a compound having the following general formula (VIII):

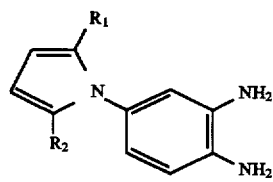

wherein $R_1$ and $R_2$ are defined as previously described, is reacted with a compound having the following general formula (IX):

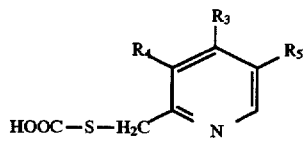

wherein $R_3$, $R_4$ and $R_5$ are defined as previously described, in a polar solvent in the presence of a strong acid.

It is a further object of the present invention to provide an antiulcerative composition containing a novel 5-pyrrolyl-2-pyridylmethylsulfinyl benzimidazole derivative as defined above.

BEST MODE FOR CARRYING OUT THE INVENTION

In one aspect, the present invention relates to a novel 5-pyrrolyl-2-pyridylmethylsulfinyl benzimidazole derivative having the following general formula (I):

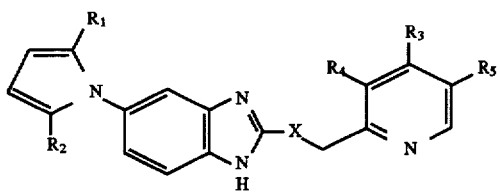

(I)

and a salt thereof, in which

X represents S, SO or $SO_2$, $R_1$ and $R_2$ independently from each other represent hydrogen or alkyl, $R_3$ represents hydrogen, $C_1$–$C_8$ alkyl, —$SR_6$, —$N(R_7)_2$, 1-piperidinyl, 4-morpholinyl, 4-methylpiperazin-1-yl, 1-pyrrolidinyl, —$OR_6$, or —$O(CH_2)_m$—Z, wherein $R_6$ represents $C_1$–$C_4$ alkyl, $C_2$–$C_4$ alkenyl, $C_3$–$C_{10}$ cycloalkyl, $C_2$–$C_5$ fluoroalkyl, or phenyl or benzyl, each of which independently substituted with one or more halogen or $C_1$–$C_4$ alkyl or alkoxy optionally substituted with halogen, $R_7$ represents hydrogen or $C_1$–$C_5$ alkyl, Z represents a group —$O(CH_2)_p$—$OR_8$, —$O(CH_2)_q$—$R_9$ or —$O(CH_2)_r O(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$–$C_5$ alkyl, or when $R_4$ and $R_5$ together with the carbon atoms adjacent to pyridine ring form a ring, $R_4$ and $R_3$ or $R_3$ and $R_5$ represent —CH=CH—CH=CH—, —$O(CH_2)_n$—, —$O(CH_2)_nO$—, —$CH_2(CH_2)_n$— or —OCH=CH— wherein n denotes an integer of 1 to 4.

The preferred compounds of formula (I) according to the present invention include those wherein X represents S, SO or $SO_2$, $R_1$ and $R_2$ independently from each other represent hydrogen or alkyl $R_3$ represents hydrogen, $C_1$–$C_8$ alkyl, —$SR_6$, —$N(R_7)_2$, 1-piperidinyl, 4-morpholinyl, 4-methylpiperazin-1-yl, 1-pyrrolidinyl, —$OR_6$, or —$O(CH_2)_m$—Z, wherein $R_6$ represents $C_1$–$C_4$ alkyl, $C_2$–$C_4$ alkenyl, $C_3$–$C_{10}$ cycloalkyl optionally substituted with $C_1$–$C_4$ alkyl, $C_2$–$C_5$ fluoroalkyl containing 3 to 8 fluorine atoms, or phenyl which is substituted with one or more halogen or $C_1$–$C_4$ alkyl or alkoxy optionally substituted with halogen, $R_7$ represents hydrogen or $C_1$–$C_5$ alkyl, Z represents a group —$O(CH_2)_p$—$OR_8$, —$O(CH_2)_q$—$R_9$ or —$O(CH_2)_r O(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$–$C_5$ alkyl, or when $R_4$ and $R_5$ together with the carbon atoms adjacent with pyridine ring form a ring, $R_4$ and $R_3$ or $R_3$ and $R_5$ represent —CH=CH—CH=CH—, —$O(CH_2)_n$—, —$CH_2(CH_2)_n$— or —OCH=CH—, wherein n denotes an integer of 2 to 4 and the oxygen atom must be present in the $R_3$ position.

In the preferred definition of $R_6$ above, $C_2$–$C_4$ alkenyl includes, for example, 1-propenyl, 3-butenyl or their isomers; and the example of C3–C10 cycloalkyl may include unsubstituted or substituted cycloalkyl, for example, cyclopropyl, 2-methylcyclopropyl, 2,2-dimethylcyclopropyl, 2,3-diethylcyclopropyl, 2-butylcyclopropyl, cyclobutyl, 2-methylcyctclobutyl, 3-propylcyclobutyl, 2,3,4-triethylcyclobutyl, 2,2-dimethylcyclohexyl, cycloheptyl, cyclooctyl, cyclononyl, cyclodecyl, etc. In addition, the example of "phenyl substituted with one or more halogen, C1–C4 alkyl or alkoxy optionally substituted with halogen" may include phenyl(o-, m- or p-)tolyl, (o-, m- or p-)ethylphenyl, 2-ethyltolyl, 4-ethyl-o-tolyl, 5-ethyl-m-tolyl, (o-, m- or p-)propylphenyl, 2-propyl-(o-, m- or p-)tolyl, 4-isopropyl-2,6-xylyl, 3-propyl-4-ethylphenyl, (2,3,4-, 2,3,6- or 2,4,5-)trimethylphenyl, (o-, m- or p-)fluorophenyl, (4-, 2,5-, 2,6-, 3,4- or 3,5-)difluorophenyl, (o-, m- or p-)chlorophenyl, 2-chloro-p-tolyl, (3-, 4-, 5- or 6-)-chloro-o-tolyl, (o-, m- or p-trifluoromethyl) phenyl, 4-fluoro- 2,5-xylyl, 4-chloro-2-propylphenyl, 2-isopropyl-4-chlorophenyl, 4-chloro-3,5-xylyl, (2,3-, 2,4-, 2,5-, 2,6- or 3,5-)dichlorophenyl, 4-chloro-3-fluorophenyl, (3- or 4-)chloro-2-fluorophenyl, (o-, m- or p-)trifluoromethylphenyl, (o-, m- or p-)ethoxyphenyl, (4- or p-(4-, or 5-)chloro-2-methoxyphenyl or 2,4-dichloro-(5- or 6-)methylphenyl. The example of "$C_2$–$C_5$ fluoroalkyl" may include 2,2,2-trifluoroethyl, 2,2,3,3,3-pentafluoropropyl, 2,2,3,3-tetrafluoropropyl, 1-(trifluoromethyl)-2,2,2-trifluoroethyl, 2,2,3,3,4,4,4-heptafluorobutyl, 2,2,3,3,4,-4,5, 5-octafluoropentyl and the like.

The more preferred compounds of formula (I) according to the present invention include those wherein X represents S, SO or $SO_2$, $R_1$ and $R_2$ independently from each other represent hydrogen or methyl, $R_3$ represents hydrogen, methyl, methoxy, ethoxy, 2,2,2-trifluoroethoxy or 3,3,3,2,2-pentafluoropropoxy, $R_4$ represents hydrogen or methyl and $R_5$ represents hydrogen, methyl or ethyl.

In addition, the most preferred compounds of formula (I) according to the present invention include those wherein X represents SO, $R_1$ and $R_2$ independently from each other represent hydrogen, $R_3$ represents methoxy or ethoxy and $R_4$ and $R_5$ independently from each other represent hydrogen, methyl or ethyl.

In another aspect, the present invention relates to a process for preparing the compound of formula (I) as defined above.

The compound of formula (I) according to the present invention can be prepared by reacting a compound of formula (II) with a compound of formula (III) in an organic solvent in the presence of a base as shown in the following reaction scheme (A):

Reaction Scheme (A)

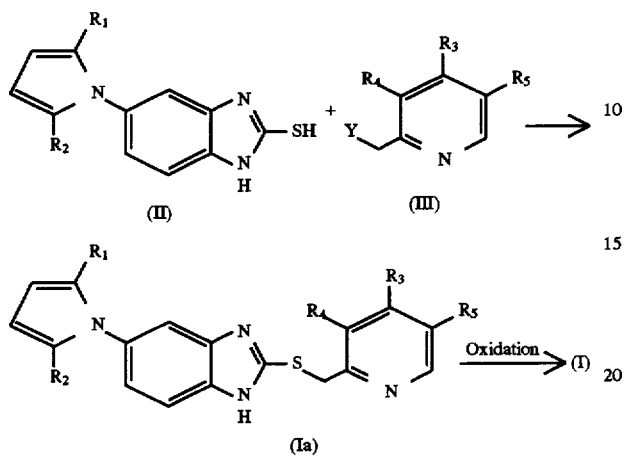

In the above reaction scheme,

X, $R_1$, $R_2$, $R_3$, $R_4$ and $R_5$ are defined as in the compound of formula (I) above, and Y represents halogen, esterified hydroxy or acyloxy.

In this reaction, the solvent which can be used may include a common organic solvent, for example, lower alkanol such as methanol, ethanol, etc., acetone, ether, tetrahydrofuran, methylene chloride, acetonitrile, dimethylsulfoxide or dimethylformamide, to which water may optionally be added. The reaction temperature is generally in the range of 0° C. to 150° C., preferably in the range of 50° C. to 100° C.

As the base for this reaction, hydroxides, carbonates or hydrides of alkali metal or alkaline earth metal, or tertiary amines can be used, of which an example includes sodium hydroxide, potassium hydroxide, potassium carbonate, calcium carbonate, sodium methoxide, sodium hydrogen carbonate, potassium hydride, sodium hydride, pyridine, triethylamine, ethyldiisopropylamine, or the like.

The compound of formula (I) according to the present invention can be prepared by oxidizing the compound of formula (Ia) with a suitable amount of an oxidizing agent, as shown in the above reaction scheme (A). In this case, the resulting compound of formula (I) can be either a sulfoxide (—SO—) compound or a sulfone (—SO$_2$—) compound depending on the kind and amount of used oxidizing agent.

The oxidizing agent which can be used for this purpose include: m-chloroperoxybenzoic acid, hydrogen peroxide, peroxyacetic acid, trifluoroperoxyacetic acid, 3,5-dinitroperoxybenzoic acid, peroxymaleic acid, vanadium pentaoxide, nitric acid, ozone, dinitrogen tetraoxide, iodoxobenzene, N-halosuccinimide, 1-chlorobenzotriazole, t-butylhypochlorite, diazabicyclo[2,2,2]octane, sodium metaperiodate, selenium dioxide, manganese dioxide, chromic acid, ceric ammonium nitrate, bromine, chlorine, sulfuryl chloride, and the like. Preferably, the reaction can be carried out in an inert solvent, for example, an aromatic hydrocarbon such as benzene or toluene; a chlorinated hydrocarbon such as chloroform or methylene chloride; or acetone.

In this case, the reaction temperature is generally in the range of −70° C. to the boiling point of the solvent used therein, preferably in the range of −50° C. to −20° C.

The compound of formula (I) according to the present invention can also be prepared by reacting a compound of formula (IV) with a compound of formula (V) as shown in the following reaction scheme (B):

Reaction Scheme (B)

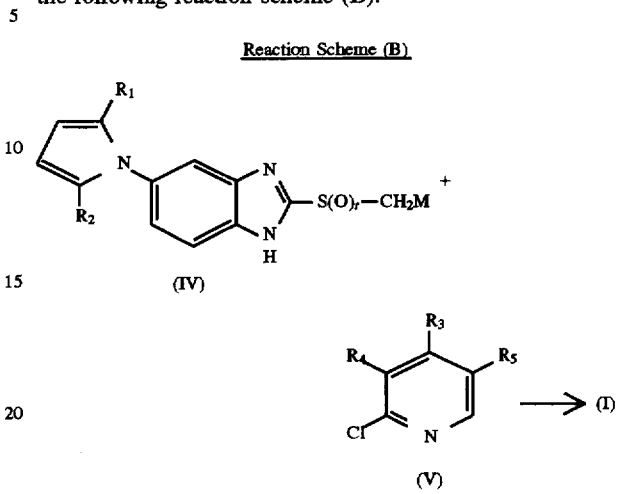

In the above reaction scheme,

X, $R_1$, $R_2$, $R_3$, $R_4$ and $R_5$ are defined as in the compound of formula (I) above, t denotes 1 or 2, and M represents an alkali metal.

This reaction can preferably be carried out in a conventional inert solvent as mentioned above. In addition, the reaction is carried out generally at the temperature of 0° C. to 120° C., preferably at the boiling point of the solvent used therein.

The compound of formula (V) which is used as the starting material in the method according to the reaction scheme (B) for preparing the compound of formula (I) of the present invention can be prepared by reacting a pyridine N-oxide intermediate with a conventional chlorinating agent such as phosphorus oxychloride, phosphorus pentachloride, and the like.

Alternatively, the compound of formula (I) according to the present invention can also be prepared by reacting a compound of formula (VI) with a compound of formula (VII) as shown in the following reaction scheme (C):

Reaction Scheme (C)

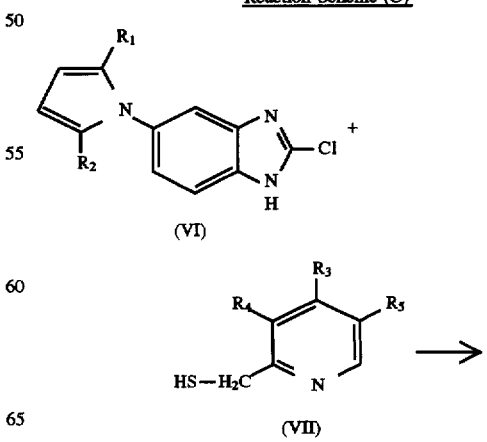

-continued

Reaction Scheme (C)

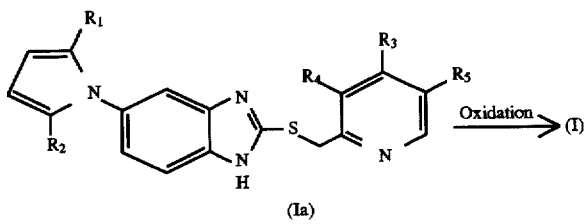

(Ia)

In the above reaction scheme X, $R_1$, $R_2$, $R_3$, $R_4$ and $R_5$ are defined as in the compound of formula (I) above.

In this reaction, the reaction conditions are substantially identical to those in the reaction according to the reaction scheme (A) for preparing the compound of formula (I) of the present invention.

In addition, the compound of formula (Ia) produced according to the above method may be oxidized under the same conditions as in the reaction scheme (A) above, to prepare the compound of formula (I) according to the present invention.

In addition, the compound of formula (I) according to the present invention can be prepared by reacting a compound of formula (VIII) with a compound of formula (IX) in a polar solvent in the presence of a strong acid, as shown in the following reaction scheme (D):

Reaction Scheme (D)

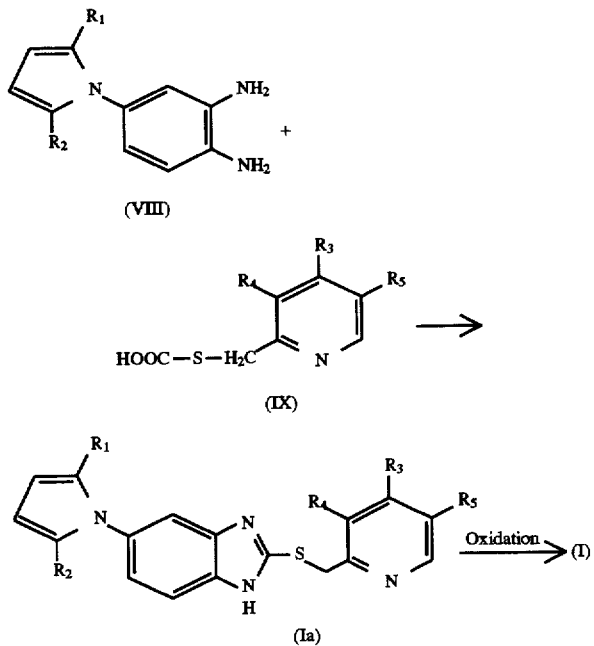

In the above reaction scheme X, $R_1$, $R_2$, $R_3$, $R_4$ and $R_5$ are defined as in the compound of formula (I) above.

In this reaction, the polar solvent may also contain water.

The reaction according to the reaction scheme (D) can be carried out at the boiling point of the solvent used therein.

The compound of formula (Ia) which can be produced according to the reaction schemes (C) and (D) may be oxidized according to the same procedure as the reaction scheme (A) to prepare the compound of formula (I) of the present invention.

The starting materials used in the above mentioned processes according to the present invention are presently known and can be prepared according to known methods.

The compound of formula (I) prepared by the above mentioned processes according to the present invention can be separated and purified according to conventional working up procedures or can be converted into a pharmaceutically acceptable salt form thereof according to conventional methods.

The compound of formula (I) according to the present invention can be used for prophylaxis and treatment of gastric and duodenal ulcers. The compound of formula (I) has a chemical structure similar to that of the known anti-ulcer agent, omeprazole, and therefore exhibits a similar pharmacological acting mechanism to that of omeprazole. Further, as demonstrated from the in vitro test, the pharmacological efficacy of the compound of formula (I) according to the present invention is about 7 times as high as that of omeprazole. In addition, in the in vivo test using animals it has also been demonstrated that the compound of formula (I) has a strong pharmacological effect 2.5 to 3 times as high as that of omeprazole.

In addition, according to the pharmacological toxicity test it has been identified that the compound of formula (I) according to the present invention has no acute toxicity or CNS toxicity.

Accordingly, the novel compound of formula (I) according to the present invention is an excellent anti-ulcer agent which has a superior pharmacological effect far better than that of any known anti-ulcer agent and also a prolonged duration of action.

The compound of formula (I) according to the present invention can be administered either per orally or parenterally. The preferred route of administration is per oral.

The compound of formula (I) according to the present invention can be administered itself or in the form of a pharmaceutically acceptable salt thereof. Suitable examples of such salts of the compound of formula (i) include an acid addition salt and an alkali metal salt. As the alkali metal salt, sodium salt, potassium salt, lithium salt, magnesium salt, calcium alt or alkylamino salt can be mentioned. As an acid which can form the acid addition salt of the compound of formula (I), the following can be mentioned: sulfuric acid, sulfonic acid, phosphoric acid, nitric acid, perchloric acid, formic acid, acetic acid, propionic acid, succinic acid, glucolic acid, lactic acid, malic acid, tartaric acid, citric acid, ascorbic acid, maleic acid, hydroxymaleic acid, pyruvic acid, phenylacetic acid, benzoic acid, p-aminobenzoic acid, p-hydroxybenzoic acid, salicylic acid, p-aminosalicylic acid, ambonic acid, methanesulfonic acid, ethanesulfonic acid, hydroxyethanesulfonic acid, ethylenesulfonic acid, toluenesulfonic acid, naphthylsulfonic acid, sulfanilic acid, camphorsulfonic acid, quinic acid, o-menylenemandelic acid, hydrogenbenzene sulfonic acid, methionine, tryptophane, lysine, arginine, picric acid or d-o-tolyl-tartaric acid.

The compound of formula (I) according to the present invention can be administered in a suitable pharmaceutically acceptable formulation which is prepared by using a pharmaceutically acceptable additive and a suitable carrier by methods well known to those skilled in the related art. Although such formulation includes various pharmaceutically acceptable formulations such as capsules, tablets, sustained release formulations, sugar-coated tablets, syrups or injections, the enteric-coated capsule or tablet formulations are preferably administered.

The compounds of this invention can be employed in admixture with conventional excipients, i.e. pharmaceutically acceptable organic or inorganic carrier substances suitable for parenteral, enteral (e.g. oral) administration which do not deleteriously react with the active compounds.

Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, and the like. The pharmaceutical preparations can be sterilized and if desired mixed with auxiliary agents, e.g., preservatives, stabilizers, emulsifiers, salts for influencing osmotic pressure, buffers, coloring, flavoring and/or aromatic substances and the like which do not deleteriously react with the active compounds. They can also be combined with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, or capsules. A syrup, elixir, or the like, can be used where a sweetened vehicle is employed.

The dosage of the compounds according to this invention generally is 1 to 1000 mg/day, preferably 3 to 100 mg/day, when administered to adult human patients for the prophylaxis and treatment of gastric and duodenal ulcers. As is appreciated by one skilled in the art, dosages can be determined using conventional considerations, e.g., by customary comparison of the differential activities of the subject compounds and of a known agent, e.g., by means of an appropriate, conventional pharmacological protocol.

The present invention will be more specifically illustrated by the following examples. However, it should be understood that the present invention will not be limited to these examples.

PREPARATION EXAMPLE

EXAMPLE 1

Preparation of 2-[[(4-methoxy-3-methyl)-2-pyridinyl]methylthio]-5-(1H-pyrrol-1-yl)-1H-benzimidazole (Compound 1)

2 g (9.3 mmole) of 5-(1H-pyrrol-1-yl)-2-mercaptobenzimidazole was dissolved in a solution of 0.74 g (2 eq. wt.) of sodium hydroxide in 100 ml of methanol at the room temperature. To the resulting solution was added 1.9 g (1 eq. wt.) of 4-methoxy-3-methyl-2-chloromethylpyridine hydrochloride and then the mixture was allowed to react for 3 hours at 50° to 60° C. and then filtered to remove the precipitated inorganic material. The solvent was removed under reduced pressure and the residue was crystallized from ether to obtain 2.7 g (85%) of the desired compound.

Melting Point: 191°–193° C.

$^1$H-NMR δ[DMSO-$d_6$]: 2.3(s, 3H), 3.9(s, 3H), 4.8 (s, 2H), 6.3 (t, 2H), 7.0 (d, 1H), 7.4 (t, 2H), 7.6(d, 1H), 7.7(s, 1H), 7.8(d, 1H), 8.3(d, 1H)

EXAMPLE 2

Preparation of 2-[[(4-methoxy-3-methyl)-2-pyridinyl]methylsulfinyl]-5-(1H-pyrrol-1-yl)-1H-benzimidazole (Compound 2)

6.7 g (19 mmole) of the compound prepared in EXAMPLE 1 was dissolved in 150ml of chloroform and then cooled down to –40° C. m-chloroperoxybenzoic acid (1 eq. wt.) dissolved in chloroform was slowly added dropwise thereto and then the mixture was stirred for 20 minutes at –40° C. The reaction mixture was diluted with chloroform and washed with sodium bicarbonate and saturated saline. The chloroform solution was dried with sodium sulfate. After removing the solvent under reduced pressure, the resulting crude product was dissolved in ethyl acetate and then crystallized with ether to obtain 5.6 g (80%) of the desired compound.

Melting Point: 122°–123° C.

$^1$H-NMR δ[DMSO-$d_6$]: 2.3(s, 3H), 3.8(s, 3H), 4.7–4.9 (dd, 2H), 6.3(t, 2H), 7.0(d, 1H), 7.4(t, 2H), 7.6(d, 1H), 7.7(s, 1H), 7.8(d, 1H), 8.3(d, 1H)

Compounds 3 to 12 listed in the following Table 1 and 2 can be prepared according to the same procedure as EXAMPLE 2.

EXAMPLE 3

Preparation of 2-[[(4-(2,2,2-trifluoroethoxy)-3-methyl)-2-pyridinyl]methylsulfinyl]-5-(1H-pyrrol-1-yl)-1H-benzimidazole (Compound 13)

2 g (9.3 mmole) of 5-(1H-pyrrol-1-yl)-2-mercaptobenzimidazole was dissolved in a solution of 0.74 g (2 eq. wt.) of sodium hydroxide in 100 ml of methanol. To the resulting solution was added 2.6 g (1 eq. wt.) of 4-(2,2,2-trifluoroethoxy)-3-methyl-2-chloromethylpyridine hydrochloride and then the mixture was allowed to react for 3 hours at 50° to 60° C. After removing the solvent under reduced pressure, the resulting product was dissolved in 150 ml of chloroform and then cooled down to –40° C. To this reaction solution was slowly added dropwise m-chloroperoxybenzoic acid (1 eq. wt.) dissolved in chloroform and then the mixture was stirred for 20 minutes at –40° C., diluted with chloroform and washed with sodium bicarbonate and saturated saline. The chloroform solution was dried with sodium sulfate. After removing the solvent under reduced pressure, the resulting crude product was dissolved in ethyl acetate and then crystallized from ether to obtain 3.6 g (88%) of the desired compound.

Melting Point: 156°–157° C.

$^1$H-NMR δ[DMSO-$d_6$]: 2.2(s, 3H), 4.3(q, 2H) , 4.6–4.9 (dd, 2H), 6.3(t, 2H), 6.6(d, 1H), 7.1(t, 2H), 7.3(d, 1H), 7.4(s, 1H), 7.7(d, 1H), 8.3 (d, 1H)

EXAMPLE 4

Preparation of 2-[[(4-(2,2,3,3,3-pentafluoropropoxy)-3-methyl)-2-pyridinyl]methylsulfinyl]-5-(1H-pyrrol-1-yl)-1H-benzimidazole (Compound 14)

2 g (9.3 mmole) of 5-(1H-pyrrol-1-yl)-2-mercaptobenzimidazole was dissolved in a solution of 0.74 g (2 eq. wt.) of sodium hydroxide in 100 ml of methanol. To the resulting solution was added 3 g (1 eq. wt.) of 4-(2,2,3,3,3-pentafluoropropoxy)-3-methyl-2-chloromethylpyridine hydrochloride and then the mixture was allowed to react for 3 hours at 50° to 60° C. After removing the solvent under reduced pressure, the resulting product was dissolved in 150 ml of chloroform and then cooled down to –40° C. To this reaction solution was slowly added dropwise m-chloroperoxybenzoic acid (1 eq. wt.) dissolved in chloroform and then the mixture was stirred for 20 minutes at –40° C., diluted with chloroform and washed with sodium bicarbonate and saturated saline. The chloroform solution was dried with sodium sulfate. After removing the solvent under reduced pressure, the resulting crude product was dissolved in ethyl acetate and then crystallized from ether to obtain 4 g (90%) of the desired compound.

Melting Point: 158°–160° C.

$^1$H-NMR δ[DMSO-d$_6$]: 2.2(s, 3H), 4.7–4.9(dd, 2H), 5.0(t, 2H), 6.3(t, 2H), 7.1(d, 1H), 7.4(t, 2H), 7.6(d, 1H), 7.7(s, 1H), 7.8(d, 1H), 8.3 (d, 1H)

EXAMPLE 5

Preparation of 2-[[(4-methoxy-3-methyl)-2-pyridinyl]methylsulfinyl]-5-(1H-2,5-dimethylpyrrol-1-yl)-1H-benzimidazole (Compound 15)

2g (8.2 mmole) of 5-(2,5-dimethylpyrrol-1-yl)-2-mercaptobenzimidazole was dissolved in a solution of 0.66 g (2 eq. wt.) of sodium hydroxide in 100 ml of methanol. To the resulting solution was added 1.7 g (1 eq. wt.) of 4-methoxy-3-methyl-2-chloromethylpyridine hydrochloride and then the mixture was allowed to react for 3 hours at 50° to 60° C. After removing the solvent under reduced pressure, the resulting product was dissolved in 150 ml of chloroform and then cooled down to −40° C. To this reaction solution was slowly added dropwise m-chloroperoxybenzoic acid (1 eq. wt.) dissolved in chloroform and then the mixture was stirred for 20 minutes at −40° C. After removing the solvent at 40° C. under reduced pressure, the residue was subjected to silica gel chromatography utilizing ethyl acetate as an eluant to obtain 1.4 g (40%) of the desired compound.

Melting Point: 94°–96° C. $^1$H-NMR δ[DMSO-d$_6$]: 1.9(s, 6H), 2.1(s, 3H), 3.8(s, 3H), 4.5–4.8(dd, 2H), 5.8(d, 2H), 6.9(d, 1H), 7.2(d, 1H), 7.4(s, 1H), 7.6(d, 1H), 8.2(d, 1H)

EXAMPLE 6

Preparation of 2-[[(4-methoxy-3-methyl)-2-pyridinyl]methylsulfinyl]-5-(1H-pyrrol-1-yl)-1H-benzimidazole sodium salt 1 g (2.7 mmole) of the compound prepared in EXAMPLE 2 was dissolved in 15 ml of methylene chloride and then 0.1 g (2.7 mmole) of sodium hydroxide dissolved in 10 ml of water was added thereto. The mixture was vigorously stirred. The aqueous layer was separated, washed several times with methylene chloride and then lyophilized to obtain 0.9 g (85%) of the desired compound.

Melting Point: 230°–232° C. $^1$H-NMR δ (D$_2$O): 2.0(s, 3H), 3.9(s, 3H), 4.5–4.9(dd, 2H), 6.4(t, 2H), 6.9(d, 1H), 7.4(t, 2H), 7.5(d, 1H), 7.7(s, 1H), 7.g(d, 1H), 8.2(d, 1H)

EXAMPLE 7

Preparation of 2-[[(4-methoxy-3-methyl)-2-pyridinyl]methylsulfinyl]-5-(1H-pyrrol-1-yl)-1H-benzimidazole (Compound 2)

2 g (7.9 mmole) of 2-(lithiummethylsulfinyl)-5-(1H-pyrrol-1-yl)benzimidazole was dissolved in 100 ml of benzene and then 1.25 g (1 eq. wt.) of 2-chloro-(4-methoxy-3-methyl)-pyridine was added thereto. The reaction mixture was refluxed for 2 hours and filtered to remove lithium chloride. After removing the solvent under reduced pressure, the resulting crude product was dissolved in ethyl acetate and then crystallized from ether to obtain 2.4 g (84%) of the desired compound.

Melting Point: 122°–123° C.

$^1$H-NMR δ(DMSO-d$_6$): 2.3(s, 3H), 3.8(s, 3H), 4.7–4.9 (dd, 2H), 6.3(t, 2H), 7.0(d, 1H), 7.4(t, 2H), 7.6(d, 1H), 7.7(s, 1H), 7.8(d, 1H), 8.3(d, 1H)

EXAMPLE 8

Preparation of 2-[[(4-methoxy-3-methyl)-2-pyridinyl]methylthio]-5-(1H-pyrrol-1-yl)-1H-benzimidazole (Compound 1)

2 g (9.2 mmole) of 4-methoxy-3-methyl-2-thiomethylpyridine was dissolved in a solution of 0.4 g (1 eq. wt.) of sodium hydroxide in 100 ml of ethanol. To the resulting solution was added 2 g (1 eq. wt.) of 2-chloro-5-(1H-pyrrol-1-yl)benzimidazole and then the reaction mixture was refluxed for 2 hours. After removing the solvent under reduced pressure, the resulting product was crystallized from ether to obtain 2.7 g (85%) of the desired compound.

Melting Point: 191°–193° C.

$^1$H-NMR δ(DMSO-d$_6$): 2.3(s, 3H), 3.9(s, 3H), 4.8(s, 2H), 6.3 (t, 2H), 7.0 (d, 1H), 7.4 (t, 2H), 7.6(d, 1H), 7.7(s, 1H), 7.8(d, 1H), 8.3(d, 1H)

EXAMPLE 9

Preparation of 2-[[(4-methoxy-3-methyl)-2-pyridinyl]methylthio]-5-(1H-pyrrol-1-yl)-1H-benzimidazole (Compound 1)

17.3 g (0.1 mole) of 2-[[2-(4-methoxy-3-methyl)pyridinyl]methylthio]formic acid and 21.3 g (1 eq. wt.) of o-[5-(1H-pyrrol-1-yl)]phenylenediamine were refluxed in 100 ml of 4N HCl for 40 minutes. The reaction mixture was cooled down and then neutralized with ammonia water. The solution was treated with active carbon and extracted with ethyl acetate. The solvent was removed under reduced pressure and the residue was crystallized from ether to obtain 8.8 g (25%) of the desired compound.

Melting Point: 191°–193° C.

$^1$H-NMR δ(DMSO-d$_6$): 2.3(s, 3H), 3.9(s, 3H), 4.8(s, 2H), 6.3 (t, 2H), 7.0 (d, 1H), 7.4 (t, 2H), 7.6(d, 1H), 7.7(s, 1H), 7.8(d, 1H), 8.3(d, 1H)

The physico-chemical properties of the compounds prepared according to the substantially same procedure as the above examples are described in the following Tables 1 and 2.

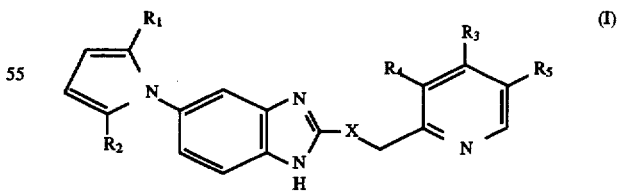

| Compound No. | X | $R_1$ | $R_2$ | $R_3$ | $R_4$ | $R_5$ | mp(°C.) | Yield (%) |
|---|---|---|---|---|---|---|---|---|
| Comp. 1 | S | H | H | $OCH_3$ | $CH_3$ | H | 191–193 | 85 |
| Comp. 2 | SO | H | H | $OCH_3$ | $CH_3$ | H | 122–123 | 80 |
| Comp. 3 | $SO_2$ | H | H | $OCH_3$ | $CH_3$ | H | 230–232 | 51 |
| Comp. 4 | SO | H | H | $OCH_3$ | $CH_3$ | $CH_3$ | 116–118 | 84 |
| Comp. 5 | SO | H | H | $OCH_3$ | H | $CH_3$ | 80–82 | 79 |
| Comp. 6 | SO | H | H | $CH_3$ | H | $CH_3$ | 90–92 | 91 |
| Comp. 7 | SO | H | H | $CH_3$ | H | H | 91–93 | 90 |
| Comp. 8 | SO | H | H | $OCH_3$ | H | H | 80 | 74 |
| Comp. 9 | SO | H | H | $OCH_2CH_3$ | $CH_3$ | H | 96–98 | 78 |
| Comp. 10 | SO | H | H | $OCH_3$ | H | $CH_2CH_3$ | 118–120 | 84 |
| Comp. 11 | SO | H | H | H | H | H | 162–164 | 93 |
| Comp. 12 | SO | H | H | H | $CH_3$ | $CH_3$ | 130–132 | 82 |
| Comp. 13 | SO | H | H | $OCH_2CF_3$ | $CH_3$ | H | 156–157 | 88 |
| Comp. 14 | SO | H | H | $OCH_2CF_2CF_3$ | $CH_3$ | H | 158–160 | 90 |
| Comp. 15 | SO | $CH_3$ | $CH_3$ | $OCH_3$ | $CH_3$ | H | 94–96 | 40 |
| Comp. 16 (Na salt) | SO | H | H | $OCH_3$ | $CH_3$ | H | 230–232 | 85 |
| Comp. 17 (K salt) | SO | H | H | $OCH_3$ | $CH_3$ | H | 248–250 | 80 |
| Comp. 18 (Na salt) | SO | H | H | $OCH_3$ | H | $CH_3$ | 232–234 | 91 |

TABLE 2

| Compound No. | $^1$H-NMR δ [DMSO-$d_6$] |
|---|---|
| 1 | 2.3(s, 3H); 3.9(s, 3H); 4.8(s, 2H); 6.3(t, 2H); 7.0(d, 1H); 7.4(t, 2H); 7.6(d, 1H); 7.7(s, 1H); 7.8(d, 1H); 8.3(d, 1H) |
| 2 | 2.3(s, 3H); 3.8(s, 3H); 4.7–4.9(dd, 2H); 6.3(t, 2H); 7.0(d, 1H); 7.4(t, 2H); 7.6(d, 1H); 7.7(s, 1H); 7.8(d, 1H); 8.3(d, 1H) |
| 3 | 2.2(s, 3H); 3.9(s, 3H); 5.1(s, 1H); 6.3(t, 2H); 7.0(d, 1H) 7.4(t, 2H); 7.6(d, 1H); 7.7(s, 1H); 7.8(d, 1H); 8.3(d, 1H) |
| 4 | 2.2(d, 6H); 3.7(s, 3H); 4.6–4.9(dd, 2H); 6.3(t, 2H); 7.0(d, 1H); 7.3(t, 2H); 7.6(t, 2H); 7.7(s, 1H); 7.8(d, 1H); 8.3(d, 1H) |
| 5 | 2.1(s, 3H); 3.7(s, 3H); 4.6–4.8(dd, 2H); 6.2(t, 2H); 6.8(s, 1H); 7.4(t, 2H); 7.6(d, 1H); 7.7(s, 1H); 7.8(d, 1H); 8.2(s, 1H) |
| 6 | 2.2–2.3(d, 6H); 4.5–4.8(dd, 2H); 6.2(t, 2H); 7.1(s, 1H); 7.3(t, 2H); 7.5(d, 1H); 7.6(s, 1H); 7.8(d, 1H); 8.3(s, 1H) |
| 7 | 2.4(s, 3H); 4.4–4.8(dd, 2H); 6.3(t, 2H); 6.9(d, 1H); 7.0(s, 1H); 7.3(t, 2H); 7.5(d, 1H); 7.6(s, 1H); 7.7(d, 1H); 8.3(s, 1H) |
| 8 | 3.7(s, 3H); 4.6–4.8(dd, 2H); 6.3(t, 2H); 6.9(s, 1H); 7.0(d, 1H); 7.4(t, 2H); 7.6(d, 1H); 7.7(s, 1H); 7.8(d, 1H); 8.3(d, 1H) |
| 9 | 1.4(t, 3H); 2.2(s, 3H); 4.1(q, 2H); 4.7–4.9(dd, 2H); 6.3(t, 2H); 7.0(d, 1H); 7.4(t, 2H); 7.6(d, 1H); 7.7(s, 1H); 7.8(d, 1H); 8.3(d, 1H) |
| 10 | 1.1(t, 3H); 2.5(q, 2H); 3.6(s, 3H); 4.6–4.8(dd, 2H); 6.2(t, 2H); 6.8(s, 1H); 7.4(t, 2H); 7.5(d, 1H); 7.6(s, 1H); 7.7(d, 1H) ; 8.2(s, 1H) |
| 11 | 4.6–4.9(dd, 2H); 6.3(t, 3H); 7.3–7.4(m, 3H); 7.5(d, 1H); 7.6(s, 1H) ; 7.7–7.9(m, 3H); 8.5(d, 1H) |
| 12 | 2.2(s, 3H); 2.3(s, 3H); 4.6–4.8(dd, 2H); 6.2(t, 2H); 7.3(t, 2H); 7.4(s, 1H); 7.5(s, 1H); 7.6(s, 1H); 7.7(d, 1H); 8.3(s, 1H) |
| 13 | 2.2(s, 3H); 4.3(q, 2H); 4.6–4.9(dd, 2H); 6.3(t, 2H); 6.6(d, 1H); 7.1(t, 2H); 7.3(d, 1H); 7.4(s, 1H); 7.7(d, 1H) 8.3(d, 1H) |
| 14 | 2.2(s, 3H); 4.7–4.9(dd, 2H); 5.0(t, 2H); 6.3(t, 2H); 7.1(d, 1H); 7.4(t, 2H); 7.6(d, 1H); 7.7(s, 1H); 7.8(d, 1H); 8.3(d, 1H) |
| 15 | 1.9(s, 6H); 2.1(s, 3H); 3.8(s, 3H); 4.5–4.8(dd, 2H); 5.8(d, 2H); 6.9(d, 1H); 7.2(d, 1H); 7.4(s, 1H); 7.6(d, 1H); 8.2(d; 1H) |
| 16 δ ($D_2O$) | 2.0(s, 3H); 3.9(s, 3H); 4.5–4.9(dd, 2H); 6.4(t, 2H); 6.9(t, 2H); 7.4(t, 2H); 7.5(d, 1H); 7.7(s, 1H); 7.8(d, 1H); 8.2(d, H) |
| 17 δ ($D_2O$) | 2.0(s, 3H); 3.9(s, 3H); 4.4–4.9(dd, 2H); 6.4(t, 2H); 6.8(d, 1H); 7.3(t, 2H); 7.5(d, 1H); 7.6(s, 1H); 7.7(d, 1H); 8.2(d, 1H) |
| 18 δ ($D_2O$) | 2.1(s, 3H); 3.2(s, 3H); 4.6–4.9(dd, 2H); 6.2(s, 1H); 6.5(t, 2H); 7.3(t, 2H); 7.4(d, 1H); 7.7(s, 1H); 7.8(d, 1H) |

Anti-ulcer effect of the compound of formula (I), as defined above, according to the present invention has been demonstrated by various experiments including the inhibition of enzyme activity, the effect of inhibition of gastric acid secretion and acidity, $ED_{50}$ and the like. The test methods and results are as follows.

PHARMACOLOGICAL TEST

TEST 1: Inhibition of enzyme activity

The inhibition of $H^+/K^+$-ATPase by the compounds of formula (I) according to the present invention was demonstrated by in vitro testing.

In this test, omeprazole [5-methoxy-2-[[(4-methoxy-3,5-dimethyl-2-pyridinyl)methyl]sulfinyl]-1H-benzimidazole] was used as the control compound.

The gastric mucous membrane was removed from a rabbit and then centrifuged with 77,000 g using a ultra-centrifuge to separate the microsomal fraction which was used as the source of $H^+/K^+$-ATPase enzyme for this test. 60 µg of $H^+/K^+$-ATPase was pre-incubated with the sample (the compound according to the present invention) for 5 minutes at 37° C. and then 4 mM ATP as the substrate and 4 mM $Mg^{++}$, 20 mM $K^+$ as the cofactor were added thereto. Then, the amount of inorganic phosphorus thus produced was determined using a spectrophotometer at 660 nm and converted into the amount of protein. The concentration of the compound which inhibits the enzyme activity by 50%, i.e. $IC_{50}$ was calculated from the percentage values for enzyme activity inhibition which were obtained from 3 to 5 test tubes containing different concentration of the sample compound, according to Litchfield-Wilcoxon method. The results thereof are described in the following Table 3.

TABLE 3

| Compound No. | $IC_{50}$ (M) | Compound No. | $IC_{50}$ (M) |
|---|---|---|---|
| 1 | >4.0 × $10^{-4}$ | 11 | >4.0 × $10^{-4}$ |
| 2 | 2.3 × $10^{-5}$ | 12 | 8.5 × $10^{-5}$ |
| 3 | >4.0 × $10^{-4}$ | 13 | 1.0 × $10^{-4}$ |
| 4 | 2.1 × $10^{-4}$ | 14 | >4.0 × $10^{-4}$ |
| 5 | 3.2 × $10^{-5}$ | 15 | 3.3 × $10^{-5}$ |
| 6 | ca. 4.0 × $10^{-4}$ | 16 | 2.8 × $10^{-5}$ |
| 7 | >4.0 × $10^{-4}$ | 17 | 1.3 × $10^{-5}$ |
| 8 | 9.1 × $10^{-5}$ | 18 | 3.8 × $10^{-5}$ |
| 9 | 6.4 × $10^{-5}$ | Omeprazole | ca. 1.6 × $10^{-4}$ |
| 10 | 8.8 × $10^{-6}$ | | |

TEST 2: Effect on inhibition of gastric juice secretion nd acidity (in vivo)

As the second in vivo test, the tests for the inhibition of gastric juice secretion and acidity were conducted with rats using the Shay method and the results were compared with the normal control group and the omeprazole group. The specific test methods are as follows.

SD male rats (200±20 g) were fasted for 24 hours, except for water, and then anesthesized with ether. The abdomen of rats was incised and then the pylorus was ligated. The test compounds were suspended or dissolved in 5% CMC (carboxymethylcellulose) and injected into duodenum. After the abdomen was sutured, the rats were allowed to stand for 5 hours and then sacrificed with ether. The stomach was removed from rats and the gastric juices were collected. The gastric juice was centrifuged with 10,000 xg for 10 minutes at 4° C. to remove the precipitate. The amount of gastric juice and acidity were determined using pH 7.0 end point assay with 0.02N NaOH and then the total acid output was calculated.

The results thereof are described in the following Table 4 and 5.

TABLE 4

Effect on inhibition of gastric juice secretion

| | Dose (mg/kg) | Number of animals | Volume (ml/100 g BW) | Inhibition rate (%) |
|---|---|---|---|---|
| Normal Group | | 6 | 3.70 ± 0.38 | — |
| Omeprazole | 10 | 6 | 1.68 ± 0.30 | 54.49 |
| Compound 2 | 3 | 6 | 1.98 ± 0.23 | 46.45 |
| | 10 | 6 | 1.31 ± 0.10 | 64.55 |
| | 30 | 6 | 0.99 ± 0.14 | 73.11 |
| Normal Group | | 6 | 2.77 ± 0.52 | — |
| Compound 5 | 10 | 6 | 1.31 ± 0.23 | 52.81 |
| | 30 | 6 | 0.99 ± 0.16 | 64.30 |
| Normal Group | | 6 | 1.99 ± 0.21 | — |
| Compound 8 | 10 | 6 | 1.42 ± 0.24 | 28.85 |
| | 30 | 6 | 0.87 ± 0.15 | 56.09 |
| Normal Group | | 6 | 2.35 ± 0.26 | — |
| Compound 9 | 10 | 6 | 1.50 ± 0.15 | 36.04 |
| | 30 | 6 | 1.14 ± 0.12 | 51.46 |
| Normal Group | | 6 | 3.50 ± 0.28 | — |
| Compound 16 | 3 | 6 | 2.05 ± 0.16 | 41.29 |
| | 10 | 5 | 1.35 ± 0.12 | 61.51 |
| | 30 | 5 | 1.17 ± 0.20 | 66.61 |
| Normal Group | | 6 | 2.89 ± 0.30 | — |
| Compound 17 | 3 | 6 | 1.31 ± 0.18 | 54.79 |
| | 10 | 6 | 1.23 ± 0.20 | 57.55 |
| | 30 | 6 | 1.15 ± 0.15 | 60.38 |

TABLE 4-continued

Effect on inhibition of gastric juice secretion

| | Dose (mg/kg) | Number of animals | Volume (ml/100 g BW) | Inhibition rate (%) |
|---|---|---|---|---|
| Normal Group | | 6 | 3.09 ± 0.55 | — |
| Compound 18 | 3 | 6 | 2.24 ± 0.12 | 27.35 |
| | 10 | 6 | 2.14 ± 0.30 | 30.90 |
| | 30 | 6 | 1.53 ± 0.19 | 50.42 |

TABLE 5

Effect on inhibition of acidity

| | Dose (mg/kg) | Number of animals | Volume (μ Eq/hr) | Inhibition rate (%) |
|---|---|---|---|---|
| Normal Group | | 6 | 77.88 ± 12.26 | — |
| Omeprazole | 10 | 6 | 12.46 ± 1.85 | 84.00 |
| Compound 2 | 3 | 6 | 31.09 ± 4.10 | 60.08 |
| | 10 | 6 | 10.20 ± 1.93 | 86.90 |
| | 30 | 6 | 5.32 ± 3.30 | 93.17 |
| Normal Group | | 6 | 57.44 ± 16.99 | — |
| Compound 5 | 10 | 6 | 16.89 ± 4.06 | 70.60 |
| | 30 | 6 | 5.59 ± 2.22 | 90.27 |
| Normal Group | | 6 | 36.46 ± 7.97 | — |
| Compound 8 | 10 | 6 | 14.29 ± 2.81 | 60.81 |
| | 30 | 6 | 2.92 ± 1.42 | 91.99 |
| Normal Group | | 6 | 27.31 ± 9.34 | — |
| Compound 9 | 10 | 6 | 11.84 ± 3.10 | 56.66 |
| | 30 | 6 | 3.80 ± 1.54 | 86.09 |
| Normal Group | | 6 | 75.42 ± 9.85 | — |
| Compound 16 | 3 | 6 | 22.59 ± 2.88 | 70.05 |
| | 10 | 5 | 10.99 ± 3.05 | 85.43 |
| | 30 | 5 | 1.98 ± 1.21 | 97.37 |
| Normal Group | | 6 | 59.82 ± 9.63 | — |
| Compound 17 | 3 | 6 | 14.94 ± 3.02 | 75.02 |
| | 10 | 6 | 8.50 ± 1.30 | 85.79 |
| | 30 | 6 | 6.06 ± 3.05 | 89.87 |
| Normal Group | | 6 | 60.87 ± 12.70 | — |
| Compound 18 | 3 | 6 | 28.37 ± 3.44 | 53.39 |
| | 10 | 6 | 23.40 ± 3.94 | 61.55 |
| | 30 | 6 | 15.72 ± 3.60 | 74.18 |

As can be seen from the above test results, among the compound of formula (I) according to the present invention Compounds 2, 4, 5, 8, 9, 10, 12, 13, 15, 16, 17 and 18 exhibit a similar or superior enzyme inhibition activity to the known anti-ulcer agent, Omeprazole, and Compounds 2, 5, 8, 9, 16 and 17 exhibit a good effects for inhibition of gastric acid secretion and for lowering acidity. Particularly, it was identified that Compounds 2 and 5 among the compound of formula (I) according to the present invention exhibit a strong inhibition of gastric juice secretion and a high acidity lowering effect even at a lower dose than that of the known anti-ulcer agent and the $ED_{50}$ of Compound 2 was 3.6 mg/kg for the effect on inhibition of gastric acid secretion and 1.6 mg/kg for the effect on inhibition of acidity.

TEST 3: Acute toxicity test

Five weeks aged ICR (male, female) mouse were pre-bred in the breeding cage for one week and then the animals showing a smooth gain in body weight were randomly selected and used in this test. The amount to be administered to the test animals was established on the basis of the maximum dose of 4,000 mg/kg with the common ratio of 1.5.

The test compounds in a powder form were suspended in 0.5% methylcellulose and administered per oral using a syringe. The other specific conditions for administration are described in the following.

| Group | Sex | Number of animals | Total dose (mg/kg) | Number of dosage per day | Dose (mg/kg) | Duration of dosage (days) |
|---|---|---|---|---|---|---|
| Control | M | 5 |  | 1 | 20 | 14 |
|  | F | 5 |  | 1 | 20 | 14 |
| G1 | M | 5 | 1,185 | 1 | 20 | 14 |
|  | F | 5 | 1,185 | 1 | 20 | 14 |
| G2 | M | 5 | 1,778 | 1 | 20 | 14 |
|  | F | 5 | 1,778 | 1 | 20 | 14 |
| G3 | M | 5 | 2,667 | 1 | 20 | 14 |
|  | F | 5 | 2,667 | 1 | 20 | 14 |
| G4 | M | 5 | 4,000 | 1 | 20 | 14 |
|  | F | 5 | 4,000 | 1 | 20 | 14 |

In the above test, the control group received only 0.5% methylcellulose.

The clinical symptoms and death of test animals caused by the test compounds were observed immediately after administration of the test compounds and during the overall test period and the change in body weight was recorded three times, i.e. on the day of administration, one week after administration and the end day of test.

After the test is completed, all the test animals were sacrificed with ether and the change in the internal and external organs due to the test compounds was observed.

From the results of this test as shown above, it can be identified that Compound 2 according to the present invention is a very safe compound which has a $LD_{50}$ value of 4,000mg/kg or more, does not affect the normal change in body weight of the test animals and further has no effect on the internal and external organs of the test animals.

TABLE 6-1

Lethality and $LD_{50}$ of Omeprazole

| Sex | Dose (mg/kg) | 0 | 1 | 2 | 3 | 4 | 5 | 6 | 7 | 8 | 9 | 10 | 11 | 12 | 13 | 14 | Lethality | $LD_{50}$ (mg/kg) |
|---|---|---|---|---|---|---|---|---|---|---|---|---|---|---|---|---|---|---|
| Male | 0 | 0 | 0 | 0 | 0 | 0 | 0 | 0 | 0 | 0 | 0 | 0 | 0 | 0 | 0 | 0 | 0/5 | 4000.0> |
|  | 1185 | 0 | 0 | 0 | 0 | 0 | 0 | 0 | 0 | 0 | 0 | 0 | 0 | 0 | 0 | 0 | 0/5 |  |
|  | 1778 | 0 | 0 | 0 | 0 | 0 | 0 | 0 | 0 | 0 | 0 | 0 | 0 | 0 | 0 | 0 | 0/5 |  |
|  | 2667 | 0 | 0 | 0 | 0 | 0 | 0 | 0 | 0 | 0 | 0 | 0 | 0 | 0 | 0 | 0 | 0/5 |  |
|  | 4000 | 0 | 0 | 0 | 0 | 0 | 0 | 0 | 0 | 0 | 0 | 0 | 0 | 0 | 0 | 0 | 0/5 |  |
| Female | 0 | 0 | 0 | 0 | 0 | 0 | 0 | 0 | 0 | 0 | 0 | 0 | 0 | 0 | 0 | 0 | 0/5 | 4000.0> |
|  | 1185 | 0 | 0 | 0 | 0 | 0 | 0 | 0 | 0 | 0 | 0 | 0 | 0 | 0 | 0 | 0 | 0/5 |  |
|  | 1178 | 0 | 0 | 0 | 0 | 0 | 0 | 0 | 0 | 0 | 0 | 0 | 0 | 0 | 0 | 0 | 0/5 |  |
|  | 2667 | 0 | 0 | 0 | 0 | 0 | 0 | 0 | 0 | 0 | 0 | 0 | 0 | 0 | 0 | 0 | 0/5 |  |
|  | 4000 | 0 | 0 | 0 | 0 | 0 | 0 | 0 | 0 | 0 | 0 | 0 | 0 | 0 | 0 | 0 | 1/5 |  |

TABLE 6-2

Lethality and $LD_{50}$ of Compound 2

| Sex | Dose (mg/kg) | 0 | 1 | 2 | 3 | 4 | 5 | 6 | 7 | 8 | 9 | 10 | 11 | 12 | 13 | 14 | Lethality | $LD_{50}$ (mg/kg) |
|---|---|---|---|---|---|---|---|---|---|---|---|---|---|---|---|---|---|---|
| Male | 0 | 0 | 0 | 0 | 0 | 0 | 0 | 0 | 0 | 0 | 0 | 0 | 0 | 0 | 0 | 0 | 0/5 | 4000.0> |
|  | 1185 | 0 | 0 | 0 | 0 | 0 | 0 | 0 | 0 | 0 | 0 | 0 | 0 | 0 | 0 | 0 | 0/5 |  |
|  | 1778 | 0 | 0 | 0 | 0 | 0 | 0 | 0 | 0 | 0 | 0 | 0 | 0 | 0 | 0 | 0 | 0/5 |  |
|  | 2667 | 0 | 0 | 0 | 0 | 0 | 0 | 0 | 0 | 0 | 0 | 0 | 0 | 0 | 0 | 0 | 0/5 |  |
|  | 4000 | 0 | 0 | 0 | 0 | 0 | 0 | 0 | 0 | 0 | 0 | 0 | 0 | 0 | 0 | 0 | 0/5 |  |
| Female | 0 | 0 | 0 | 0 | 0 | 0 | 0 | 0 | 0 | 0 | 0 | 0 | 0 | 0 | 0 | 0 | 0/5 | 4000.0> |
|  | 1185 | 0 | 0 | 0 | 0 | 0 | 0 | 0 | 0 | 0 | 0 | 0 | 0 | 0 | 0 | 0 | 0/5 |  |
|  | 1178 | 0 | 0 | 0 | 0 | 0 | 0 | 0 | 0 | 0 | 0 | 0 | 0 | 0 | 0 | 0 | 0/5 |  |
|  | 2667 | 0 | 0 | 0 | 0 | 0 | 0 | 0 | 0 | 0 | 0 | 0 | 0 | 0 | 0 | 0 | 0/5 |  |
|  | 4000 | 0 | 0 | 0 | 0 | 0 | 0 | 0 | 0 | 0 | 0 | 0 | 0 | 0 | 0 | 0 | 1/5 |  |

What is claimed is:

1. A compound having the following formula (I),

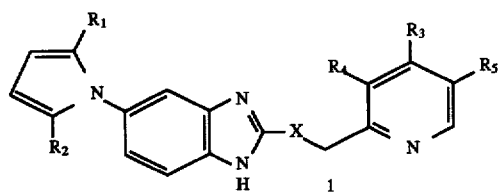

or a salt thereof, in which

X represents S, SO or SO$_2$,

R$_1$ and R$_2$ independently from each other represent hydrogen or alkyl,

R$_3$ represents hydrogen, C$_1$–C$_8$ alkyl, —SR$_6$, —N(R$_7$)$_2$, 1-piperidinyl, 4-morpholinyl, 4-methylpiperazin-1-yl, 1-pyrrolidinyl, —OR$_6$, or —O(CH$_2$)$_m$—Z, wherein R$_6$ represents C$_1$–C$_4$ alkyl, C$_2$–C$_4$ alkenyl, C$_3$–C$_{10}$ cycloalkyl, C$_2$–C$_5$ fluoroalkyl, or phenyl or benzyl, each of which independently is substituted with one or more halogen or C$_1$–C$_4$ alkyl or alkoxy optionally substituted with halogen, R$_7$ represents hydrogen or C$_1$–C$_5$ alkyl, Z represents a group —O(CH$_2$)$_p$—OR$_8$, —O(CH$_2$)$_q$—R$_9$or —O(CH$_2$)$_r$,O(CH$_2$)$_s$—OR$_{10}$, wherein p and q independently from each other denote an integer of 1 to 3, r and s independently from each other denote an integer of 1 to 5, R$_8$ represents hydrogen, lower alkyl, aryl or aralkyl, R$_9$ represents hydrogen alkoxycarbonyl, or aryl, and R10 represents hydrogen or lower alkyl, m represents an integer of 2 to 10, and R$_4$ and R$_5$ independently from each other represent hydrogen or C$_1$–C$_5$ alkyl.

2. The compound of formula (I) as defined in claim 1, wherein

X represents S, SO or SO$_2$,

R$_1$ and R$_2$ independently from each other represent hydrogen or methyl,

R$_3$ represents hydrogen, C$_1$–C$_8$ alkyl, —SR$_6$, —N(R$_7$)$_2$, 1-piperidinyl, 4-morpholinyl, 4-methylpiperzain-1-yl, 1-pyrrolidinyl, —OR$_6$, or —O(CH$_2$)$_m$—Z, wherein R$_6$ represents C$_1$–C$_4$ alkyl, C$_3$–C$_4$ alkenyl, C$_3$–C$_{10}$ cycloalkyl optionally substituted with C$_1$–C$_4$ alkyl, C$_2$–C$_5$ fluoroalkyl having 3 to 8 fluorine atoms, or phenyl or benzyl, each of which independently is substituted with one or more halogen or C$_1$–C$_4$ alkyl or alkoxy optionally substituted with halogen, R$_7$ represents hydrogen or C$_1$–C$_4$ alkyl, Z represents a group —O(CH$_2$)$_p$—OR$_8$, —O(CH$_2$)$_q$—R$_9$ or —O(CH$_2$)$_r$,O(CH$_2$)$_s$—OR$_{10}$, wherein p and q independently from each other denote an integer of 1 to 3, r and s independently from each other denote an integer of 1 to 5, R$_8$ represents hydrogen, lower alkyl, aryl or aralkyl, R$_9$ represents hydrogen alkoxycarbonyl, or aryl, and R$_{10}$ represents hydrogen or lower alkyl, m represents an integer of 2 to 10, and R$_4$ and R$_5$ independently from each other represent hydrogen or C$_1$–C$_5$ alkyl.

3. The compound of formula (I) as defined in claim 2, wherein

X represents S, SO or SO$_2$,

R$_1$ and R$_2$ independently from each other represent hydrogen or methyl,

R$_3$ represents hydrogen, methyl, methoxy, ethoxy, 2,2,2-trifluoroethoxy or 3,3,3,2,2-pentafluoropropoxy, R$_4$ represents hydrogen or methyl, and R$_5$ represents hydrogen, methyl or ethyl.

4. The compound of formula (I) as defined in claim 1, wherein

X represents SO,

R$_1$ and R$_2$ independently from each other represent hydrogen,

R$_3$ represents methoxy or ethoxy, and

R$_4$ and R$_5$ independently from each other represent hydrogen, methyl or ethyl.

5. An anti-ulcer composition comprising an effective amount of a compound having the following formula (I) as an active ingredient:

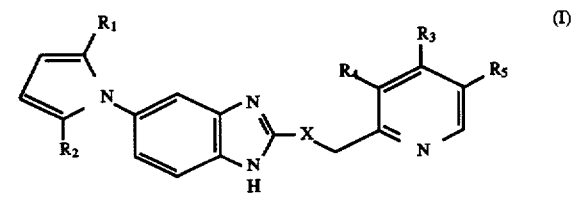

in which

X, R$_1$, R$_2$, R$_3$, R$_4$ and R$_5$ are defined as described in claim 1 for the compound of formula (I), together with a pharmaceutically acceptable carrier, adjuvant or excipient therefor.

* * * * *